(12) United States Patent
Donovan

(10) Patent No.: US 8,383,102 B2
(45) Date of Patent: Feb. 26, 2013

(54) FUSION OF PEPTIDOGLYCAN HYDROLASE ENZYMES TO A PROTEIN TRANSDUCTION DOMAIN ALLOWS ERADICATION OF BOTH EXTRACELLULAR AND INTRACELLULAR GRAM POSITIVE PATHOGENS

(75) Inventor: David Donovan, Baltimore, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 400 days.

(21) Appl. No.: 12/784,675

(22) Filed: May 21, 2010

(65) Prior Publication Data

US 2011/0027249 A1  Feb. 3, 2011

Related U.S. Application Data

(60) Provisional application No. 61/216,779, filed on May 21, 2009.

(51) Int. Cl.
*A61K 38/54* (2006.01)
*C07H 21/04* (2006.01)
*C12N 15/63* (2006.01)
*C12N 5/10* (2006.01)

(52) U.S. Cl. ....... 424/94.3; 435/188; 435/455; 435/325; 435/320.1; 536/23.2

(58) Field of Classification Search .................... None
See application file for complete search history.

(56) References Cited

PUBLICATIONS

Donovan et al "Peptidoglycan hydrolase fusions maintain their parental specificities". Applied and Environmental Microbiology Apr. 2006 vol. 72 No. 4 2988-2996.*
Kokai-Kun et al (Journal of antimicrobial Chemotherapy (2007) 60, 1051-1059 Lysostaphin as a treatment for systemic *Staphylococcus aureus* infection in a mouse model.*
Hilary Brooks et al (Tat peptide-mediated cellular delivery: back to basics Advanced Drug Delivery Reviews vol. 57, Issue 4, Feb. 28, 2005, pp. 559-577).*
Jaspal K. Kumar 9Lysostaphin: an antistaphylococcal agent (Appl Microbiol Biotechnol (2008) 80:555-561).*

* cited by examiner

*Primary Examiner* — Kagnew H Gebreyesus
(74) *Attorney, Agent, or Firm* — John D. Fado; Evelyn M. Rabin

(57) ABSTRACT

Lysostaphin is a bacteriocin secreted by *S. simulans* to kill *S. aureus*, and has been shown to also be a potent antimicrobial for many antibiotic-resistant strains of *S. aureus*. By adding a ~13 amino acid protein transduction domain (PTD) from the HIV-TAT protein to lysostaphin to form lysostaphin-PTD, both extracellular and intracellular forms of *S. aureus* and MRSA are killed in all (multiple) cell types examined.

15 Claims, 7 Drawing Sheets

FIG. 7

SEQUENCE LISTING

```
<160> NUMBER OF SEQ ID NOS: 5

<210> SEQ ID NO 1
<211> LENGTH: 795
<212> TYPE: DNA
<213> ORGANISM: Artificial Sequence
<220> FEATURE:
<223> OTHER INFORMATION: Fusion Nucleotide = Staphylococcus simulans &
      Human immunodeficiency virus

<400> SEQUENCE: 1
```

```
atggctgcaa cacatgaaca ttcagcacaa tggttgaata attacaaaaa aggatatggt      60
tacggcccct atccattagg tataaatggc ggtatgcact acggagttga ttttttatg      120 aatattggaa caccagtaaa agctatttca agcggaaaaa tagttgaagc tggttggagt     180
aattacggag gaggtaatca aataggtctt attgaaaatg atggagtgca tagacaatgg     240
tatatgcatc taagtaaata taatgttaaa gtaggagatt atgtcaaagc tggtcaaata     300
atcggttggt ctggaagcac tggttattct acagcaccac atttacactt ccaaagaatg     360
gttaattcat tttcaaattc aactgcccaa gatccaatgc ctttcttaaa gagcgcagga     420
tatggaaaag caggtggtac agtaactcca acgccgaata caggttggaa aacaaacaaa     480
tatggcacac tatataaatc agagtcagct agcttcacac ctaatacaga tataataaca     540
agaacgactg gtccatttag aagcatgccg cagtcaggag tcttaaaagc aggtcaaaca     600
attcattatg atgaagtgat gaaacaagac ggtcatgttt gggtaggtta tacaggtaac     660
agtggccaac gtatttactt gcctgtaaga acatggaata agtctactaa tactctgggt     720
gttctgtggg gaactataaa gcgcaaaaaa cgccgccagc gccgccgcct cgagcaccac     780
caccaccacc actga                                                      795
```

<210> SEQ ID NO 2
<211> LENGTH: 264
<212> TYPE: PRT
<213> ORGANISM: Artificial Sequence
<220> FEATURE:
<223> OTHER INFORMATION: Fusion Protein = Staphylococcus simulans &
      Human immunodeficiency virus

<400> SEQUENCE: 2

```
Met Ala Ala Thr His Glu His Ser Ala Gln Trp Leu Asn Asn Tyr Lys
1               5                   10                  15

Lys Gly Tyr Gly Tyr Gly Pro Tyr Pro Leu Gly Ile Asn Gly Gly Met
            20                  25                  30

His Tyr Gly Val Asp Phe Phe Met Asn Ile Gly Thr Pro Val Lys Ala
        35                  40                  45

Ile Ser Ser Gly Lys Ile Val Glu Ala Gly Trp Ser Asn Tyr Gly Gly
    50                  55                  60

Gly Asn Gln Ile Gly Leu Ile Glu Asn Asp Gly Val His Arg Gln Trp
65                  70                  75                  80

Tyr Met His Leu Ser Lys Tyr Asn Val Lys Val Gly Asp Tyr Val Lys
                85                  90                  95

Ala Gly Gln Ile Ile Gly Trp Ser Gly Ser Thr Gly Tyr Ser Thr Ala
            100                 105                 110

Pro His Leu His Phe Gln Arg Met Val Asn Ser Phe Ser Asn Ser Thr
        115                 120                 125

Ala Gln Asp Pro Met Pro Phe Leu Lys Ser Ala Gly Tyr Gly Lys Ala
    130                 135                 140

Gly Gly Thr Val Thr Pro Thr Pro Asn Thr Gly Trp Lys Thr Asn Lys
145                 150                 155                 160

Tyr Gly Thr Leu Tyr Lys Ser Glu Ser Ala Ser Phe Thr Pro Asn Thr
                165                 170                 175

Asp Ile Ile Thr Arg Thr Thr Gly Pro Phe Arg Ser Met Pro Gln Ser
            180                 185                 190

Gly Val Leu Lys Ala Gly Gln Thr Ile His Tyr Asp Glu Val Met Lys
        195                 200                 205

Gln Asp Gly His Val Trp Val Gly Tyr Thr Gly Asn Ser Gly Gln Arg
```

```
            210                 215                 220
Ile Tyr Leu Pro Val Arg Thr Trp Asn Lys Ser Thr Asn Thr Leu Gly
225                 230                 235                 240

Val Leu Trp Gly Thr Ile Lys Arg Lys Arg Arg Gln Arg Arg
                245                 250                 255

Leu Glu His His His His His His
            260

<210> SEQ ID NO 3
<211> LENGTH: 768
<212> TYPE: DNA
<213> ORGANISM: Staphylococcus simulans

<400> SEQUENCE: 3
atggctgcaa cacatgaaca ttcagcacaa tggttgaata attacaaaaa aggatatggt      60
tacggccctt atccattagg tataaatggc ggtatgcact acggagttga ttttttatg     120 aatattggaa caccagtaaa agctatttca agcggaaaaa tagttgaagc tggttggagt     180
aattacggag gaggtaatca aataggtctt attgaaaatg atggagtgca tagacaatgg     240
tatatgcatc taagtaaata taatgttaaa gtaggagatt atgtcaaagc tggtcaaata     300
atcggttggt ctggaagcac tggttattct acagcaccac atttacactt ccaaagaatg     360
gttaattcat tttcaaattc aactgcccaa gatccaatgc ctttcttaaa gagcgcagga     420
tatggaaaag caggtggtac agtaactcca acgccgaata caggttggaa aacaaacaaa     480
tatggcacac tatataaatc agagtcagct agcttcacac taatacagat ataataaca     540 agaacgactg gtccatttag aagcatgccg cagtcaggag tcttaaaagc aggtcaaaca     600
attcattatg atgaagtgat gaaacaagac ggtcatgttt gggtaggtta tacaggtaac     660
agtggccaac gtatttactt gcctgtaaga acatggaata agtctactaa tactctgggt     720
gttctgtggg gaactataaa gctcgagcac caccaccacc accactga                 768

<210> SEQ ID NO 4
<211> LENGTH: 255
<212> TYPE: PRT
<213> ORGANISM: Staphylococcus simulans

<400> SEQUENCE: 4

Met Ala Ala Thr His Glu His Ser Ala Gln Trp Leu Asn Asn Tyr Lys
1               5                   10                  15

Lys Gly Tyr Gly Tyr Gly Pro Tyr Pro Leu Gly Ile Asn Gly Gly Met
            20                  25                  30

His Tyr Gly Val Asp Phe Phe Met Asn Ile Gly Thr Pro Val Lys Ala
        35                  40                  45

Ile Ser Ser Gly Lys Ile Val Glu Ala Gly Trp Ser Asn Tyr Gly Gly
    50                  55                  60

Gly Asn Gln Ile Gly Leu Ile Glu Asn Asp Gly Val His Arg Gln Trp
65                  70                  75                  80

Tyr Met His Leu Ser Lys Tyr Asn Val Lys Val Gly Asp Tyr Val Lys
                85                  90                  95

Ala Gly Gln Ile Ile Gly Trp Ser Gly Ser Thr Gly Tyr Ser Thr Ala
            100                 105                 110

Pro His Leu His Phe Gln Arg Met Val Asn Ser Phe Ser Asn Ser Thr
        115                 120                 125

Ala Gln Asp Pro Met Pro Phe Leu Lys Ser Ala Gly Tyr Gly Lys Ala
    130                 135                 140
```

-continued

```
Gly Gly Thr Val Thr Pro Thr Pro Asn Thr Gly Trp Lys Thr Asn Lys
145                 150                 155                 160

Tyr Gly Thr Leu Tyr Lys Ser Glu Ser Ala Ser Phe Thr Pro Asn Thr
                165                 170                 175

Asp Ile Ile Thr Arg Thr Thr Gly Pro Phe Arg Ser Met Pro Gln Ser
            180                 185                 190

Gly Val Leu Lys Ala Gly Gln Thr Ile His Tyr Asp Glu Val Met Lys
            195                 200                 205

Gln Asp Gly His Val Trp Val Gly Tyr Thr Gly Asn Ser Gly Gln Arg
        210                 215                 220

Ile Tyr Leu Pro Val Arg Thr Trp Asn Lys Ser Thr Asn Thr Leu Gly
225                 230                 235                 240

Val Leu Trp Gly Thr Ile Lys Leu Glu His His His His His His
                245                 250                 255

<210> SEQ ID NO 5
<211> LENGTH: 51
<212> TYPE: DNA
<213> ORGANISM: Artificial Sequence
<220> FEATURE:
<223> OTHER INFORMATION: Chemically Synthesized

<400> SEQUENCE: 5
gtggtgctcg aggcggcggc gctggcggcg tttttttgcgc tttatagttc c         51
```

FUSION OF PEPTIDOGLYCAN HYDROLASE ENZYMES TO A PROTEIN TRANSDUCTION DOMAIN ALLOWS ERADICATION OF BOTH EXTRACELLULAR AND INTRACELLULAR GRAM POSITIVE PATHOGENS

REFERENCE TO RELATED APPLICATION

This application claims the benefit of U.S. Provisional Application No. 61/216,779, filed May 21, 2009, which is incorporated herein by reference in its entirety.

BACKGROUND OF THE INVENTION

1. Field of the Invention

This invention relates to a pathogen-specific fusion protein comprising a peptidoglycan hydrolase, lysostaphin, and a protein transduction domain. The lysostaphin specifically degrades the peptidoglycan cell wall of *S. aureus* including methicillin-resistant *Staphylococcus aureus* (MRSA). In addition to lysing bacterial cells in broth, fusion of a protein transduction domain to a peptidoglycan hydrolase enzyme allows delivery of such protein antimicrobials to the intracellular locations of persistent pathogens. These staphylococcal antimicrobials have both extracellular and intracellular activity. They can be used to treat chronic staphylococcal mastitis, and any disease caused by intracellular *S. aureus* (e.g. MRSA osteomyelitis).

2. Description of the Relevant Art

Bovine intramammary infections are caused primarily by bacterial pathogens. *S. aureus* is transmitted from cow to cow usually during milking through contaminated equipment, milker's hands, fomites, or flies, with approximately 10% of USA dairy cattle having an intramammary infection. Control programs devised in the 1960's based on teat disinfection, antibiotic therapy and culling of chronically infected cows have led to considerable progress in controlling contagious mastitis pathogens. However, *S. aureus* infections are chronic and prone to a high frequency of treatment failures. Treatment failures result from deep-seated intramammary abscesses, resistance to antibacterials, and intracellular survival of the pathogen. *S. aureus* also has numerous extracellular defenses to evade the host immune system. Biofilm formation is also believed to contribute to antimicrobial resistance (Fox et al. 2005. *Vet. Microbiol.* 107: 295-299).

Upon entry into the mammary gland, *S. aureus* interacts with either epithelial cells or phagocytic immune cells which leads to its internalization. *S. aureus* exhibits very active intracellular replication often with the induction of small colony variants. The small colony variants are phenotypically very different from the parent strain. These variants can survive environmental insults, (pH, temperature, osmolarity), and show increased resistance to cationic antimicrobial peptides, increased expression of "intracellular induction factors" fibrinogen-binding clumping factor and fibronectin-binding proteins, and intracellularly, have less exposure to the immune system. Small colony variants also have a decreased production of α-toxin, lyse fewer host cells, and produce lower amounts of toxic shock syndrome toxin 1 (TSST-1), which results in less activation of host cell mediated cytotoxicity. These features plus high resistance to aminoglycosides make small colony variants a bacterial prototype for intracellular persistence (Proctor et al. 2006. *Nat. Rev. Microbiol.* 4: 295-305; Horsburgh et al. 2002. *J. Bacteriol.* 184: 5457-5467; Vaudaux et al. 2002. *Infect. Immun.* 70: 5428-5437; Peterson et al. 2006. *Biochemistry* 45: 2387-2397).

In the absence of pathogen-specific antimicrobials, treatment of mastitis has historically been limited to the use antibiotics such as tetracycline, penicillin, and pirlimycin which are often less than 50% successful (Deluyker et al. 2005. *J. Dairy Sci.* 88: 604-614). The Middleton lab achieved a 90% cure three days after treatment with eight consecutive daily doses of intramammary pirlimycin, but this cure rate was reduced to 8% at 28d post-treatment presumably due to recrudescence of infections from intracellular reservoirs (Luby et al. 2005. *Vet. Rec.* 157: 89-90). Vaccines have been ineffective. The complexity and variety of virulence factors as well as the diversity of strains that cause intramammary infections hamper the development of effective vaccines. Results of efficacy trials on the only commercially available bovine mastitis vaccine have shown limited efficacy (Middleton et al., 2008. *Expert. Rev. Vaccines* 7: 805-815). Several lines of research using novel approaches to *S. aureus* vaccination have been investigated, but the results of in vivo efficacy trials in large mammals have not yielded promising results. Survival of *S. aureus* inside mammary cells might explain the lack of efficacy of vaccination. In addition, the ability of *S. aureus* capsular material to mask surface protein epitopes hampers antibody and complement binding making the use of cell wall antigen vaccines questionable (Middleton et al., supra).

Peptidoglycan is the major structural component of the bacterial cell wall. Autolytic peptidoglycan hydrolases alter the peptidoglycan allowing bacteria to grow and divide. Bacteriophage (viruses that infect bacteria) use peptidoglycan hydrolases (endolysins) to degrade the cell wall allowing nascent phage to escape during the phage lytic cycle. Gram-positive bacteria exposed to purified phage lysins externally undergo exolysis or "lysis from without."

Figure 1:
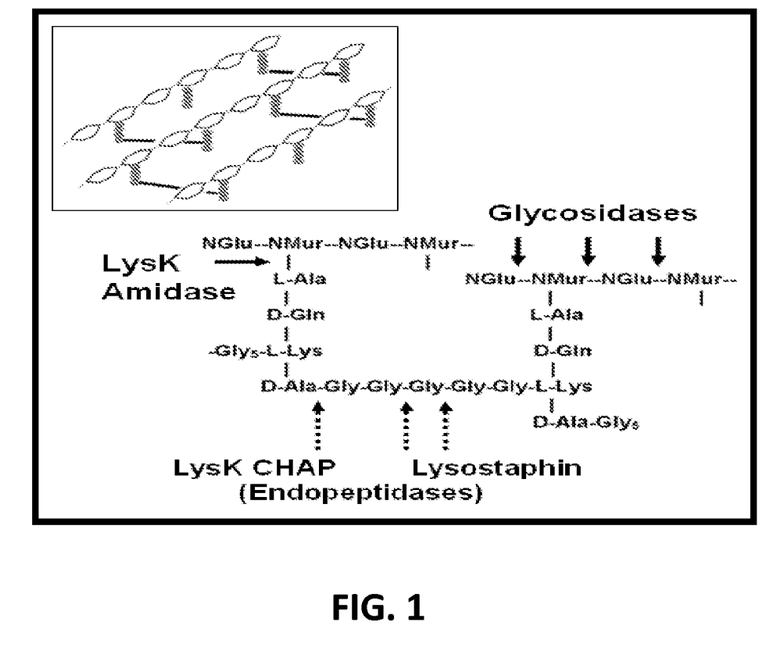
FIG. 1 depicts peptidoglycan structure and sites of hydrolase cleavage. S. aureus peptidoglycan is depicted with the generic cut sites for amidases and lysozyme-like glycosidases. Glucosaminidase and muramidase are examples of glycosidases that cleave between N-acetyl glucosamine (NGlu) and N-acetyl muramic acid (NMur). Amidases cleave between the NMur and the first amino acid of the peptide. The cut sites for LysK and lysostaphin have been determined, and are noted. Inset: Gram positive cell walls can have 40 layers of this sugar-protein structure. Figure adapted from Navarre et al., (1999. J. Biol. Chem. 274: 15847-15856).

Peptidoglycan is unique to bacteria and has a complex structure with a sugar backbone of alternating units of N-acetyl glucosamine (NGlu) and N-acetylmuramic acid (NMur). Each NMur residue is amide-linked to a short pentapeptide chain. Characteristic of *S. aureus* is the pentaglycine bridge that connects the L-Lys of the stem peptide to the D-Ala at position 4 of a neighboring subunit (FIG. 1). Peptidoglycan hydrolases have evolved a modular design with lytic (~100-200 amino acids), and SH3b cell wall binding domains (~40-60 amino acids) to deal with this complexity (Loessner et. al. 2005. *Cuff. Opin. Microbiol.* 8: 480-487). Bacteria use autolysins to modify their peptidoglycan to allow the cell to grow and divide.

Three classes of peptidoglycan hydrolase domains have been identified: endopeptidases, amidases, and glycosidases (includes glucosaminidase and lysozyme-like muramidases) (Lopez et al. 2004. *FEMS Microbiol. Rev.* 28: 553-580; FIG. 1). Alignment of conserved domain sequences has identified non-variant amino acid positions that, when mutated, can destroy the hydrolytic activity of some domains (Pritchard et al. 2004. *Microbiology* 150: 2079-2087; Huard at al. 2003. *Microbiology* 149: 695-705; Bateman et al. 2003. *Trends Biochem. Sci.* 28: 234-237; Rigden et al. 2003. *Trends. Biochem. Sci.* 28: 230-234). Chimeric peptidoglycan hydrolases have been created by the exchange of cell wall binding domains (Croux et al. 1993. *Mol. Microbiol.* 9: 1019-1025). Enzymatic activity was retained and regulatory properties exchanged when the cell wall binding domains were swapped. Intra-generic chimeric fusion lysins are also functional (Diaz et al., 1990. *Proc. Natl. Acad. Sci. USA* 87: 8125-8129; Donovan et al. 2006. *Appl. Environ. Microbiol.* 72: 2988-2996).

The most well studied peptidoglycan hydrolase is lysostaphin. Lysostaphin is a bacteriocin secreted by *S. simulans* that lyses *S. aureus* (Browder et al. 1965. *Biochem. BioPhys. Res. Comm.* 19: 383-389). The endopeptidase activity is specific to the glycyl-glycine bonds of the staphylococcal peptidoglycan inter-peptide bridge (FIG. 1). It is known that lysostaphin can kill planktonic *S. aureus* (Walencka et al. 2005. *Pol. J. Microbiol.* 54:191-200; Wu et al. 2003. *Antimicrob. Agents Chemother.* 47: 3407-3414), MRSA (Dajcs et al. 2000. *Am. J. Opthalmol.* 130: 544), antibiotic-resistant strains (Patron et al. 1999. *Antimicrob. Agents Chemother.* 43:1754-1755; Peterson et al. 1978. *J. Clin. Invest.* 61: 597-609), cells growing in a biofilm (Walencka, supra; Wu, supra), and it exhibits limited activity against coagulase negative staphylococci (CoNS; Cisani et al. 1982. *Antimicrob. Agents Chemother.* 21:531-535; McCormick et al. 2006b. *Curr. Eye Res.* 31:225-230).

Lysostaphin and other peptidoglycan hydrolases can cure mastitis and other infections and do not raise an adverse immune response. Lysostaphin has been used to treat bovine mastitis (Oldham and Daley. 1991. *J. Dairy Sci.* 74: 4175-4182). Repeated 100 μg IM doses in PBS during lactation were deemed sufficient and effectively cleared the milk of *S. aureus*, with no deleterious effects. This treatment cured 20 percent of the cattle while approximately 50 percent were cured with antibiotic treatments. Nonetheless, many treated quarters relapsed after treatment with either lysostaphin or antibiotic treatments ceased. The authors believed this was due to chronic intracellular infections. Dry cow treatments should avoid the flushing of therapeutic agents that presumably occurred during lactation in the 1991 study. Curing of *S. aureus*-challenged mammary glands was also achieved via transgenic expression of lysostaphin in milk of mice (Kerr et al., 2001. *Nat. Biotechnol.* 19: 66-70) and cows Wall et al. 2005. *Nat. Biotechnol.* 23: 445-451). Lysostaphin at 10 μg/ml was sufficient to protect the transgenic dairy cattle from the *S. aureus* challenge. However, higher levels of lysostaphin are expected to be required as a dry cow intramammary treatment than as a transgene due to reports that less transgene expression (human lysozyme) is required to afford the same level of protection in milk than would be required if added exogenously (Maga et al. 2006. *Foodborne. Pathog. Dis.* 3: 384-392).

In 1992, intramammary infusions of lysostaphin did not elicit significant serum titers in the bovine until 18-21 infusions were administered, reflecting 2-3 g of total protein being administered. These antibodies were not inactivating, did not eliminate the antimicrobial properties of the enzyme, nor elicit any observable effects on the host animal (Daley and Oldham. 1992. *Vet. Immunol. Immunopathol.* 31:301-312). Results of in vitro studies have also indicated that serum antibodies raised to phage endolysins specific to *Bacillus anthracis, Streptococcus pyogenes*, or *Streptococcus pneumoniae* slowed, but did not block, in vivo killing of the target microbe in mouse models (Fischetti, V. A. 2005. *Trends Microbiol.* 13: 491-496; Loeffler and Fischetti. 2003. *Antimicrob. Agents Chemother.* 47: 375-377). Although a reduced immune response would be expected from mucosal applications, mucosal clearing of streptococci has also been obtained with phage lytic enzymes applied to the murine vagina, oropharynx (Cheng et al. 2005. *Antimicrob. Agents Chemother.* 49: 111-117) and oral cavity (Nelson et al. 2001. *Proc. Natl. Acad. Sci. USA* 98: 4107-4112).

Although untested in cattle, the staphylococcal phage lysins phiH5 (Obeso et al. 2008. *Int. J. Food Microbiol.* 128: 212-218) and LysK (data not shown) can kill *S. aureus* ex vivo in milk.

*Staphylococcus simulans* produces lysostaphin and avoids its lytic action by the product of the lysostaphin immunity factor (lif) gene the same as the lysostaphin endopeptidase resistance (epr) gene (DeHart et al. 1995. *Appl. Environ. Microbiol.* 61: 1475-1479) that resides on a native plasmid (pACK1) (Thumm et al. 1997. *Mol. Microbiol.* 23: 1251-1265). The lif gene product inserts serine residues into the peptidoglycan cross bridge, interfering with the ability of the glycyl-glycine endopeptidase to recognize and cleave this structure (FIG. 1). Similarly, mutations in the *S. aureus* femA gene (Sugai et al. 1997. *J. Bacteriol.* 179: 4311-4318) reduce the peptidoglycan interpeptide cross bridge from pentaglycine to a single glycine, rendering *S. aureus* resistant to the lytic action of lysostaphin. MRSA using this mechanism have been identified (Climo et al. 2001. *Antimicrob. Agents Chemother.* 45: 1431-1437).

Grundling at al. identified the lyrA gene that, when mutated by a transposon insertion, reduced *S. aureus* susceptibility to lysostaphin, by ~2× (Grundling et al. 2006. *J. Bacteriol.* 188: 6286-6297). Although some structural changes were noted in peptidoglycan from the mutant, the purified peptidoglycan was susceptible to lysostaphin and the phi11 endolysin, suggesting that changes in accessibility of the enzyme to its substrate likely explain the lysostaphin resistance.

Despite the resistance to lysostaphin that is known to occur, those resistant mutants (femA) when examined in vivo and in vitro, were five-fold less virulent than their non-resistant counterparts. The mutant peptidoglycan rendered the mutants much more susceptible to and were readily curable with β-lactam antibiotics (Kusuma of al. 2007. *Antimicrob. Agents Chemother.* 51: 475-482).

Antibiotic resistance and staphylococcal biofilms contribute to mastitis. There is increasing evidence suggesting that the lack of antibiotic sensitivity observed for mastitis causing-*S. aureus* is due to biofilm formation (Fox et al., supra; Melchior et al. 2007. *Vet. Microbiol.* 125: 141-149). Lysostaphin is known to kill *S. aureus* in biofilms. Biofilms are sessile forms of bacterial colonies that attach to a mechanical or prosthetic device or a layer of mammalian cells. The National Institutes of Health (NIH) estimates that 80% of bacterial infections occur as biofilms (NIH Grants Guide 2009. Retrieved from the Internet:. Bacteria in biofilms can be orders of magnitude more resistant to antibiotic treatment than their planktonic (liquid culture) counterparts (Amorena et al. 1999. *J. Antimicrob. Chemother.* 44: 43-55; Davies, D. 2003. *Nat. Rev. Drug Discov.* 2: 114-122).

Several mechanisms are thought to contribute to the antimicrobial resistance associated with biofilms: 1) delayed or restricted penetration of antimicrobial agents through the biofilm exopolysaccharide matrix; 2) decreased metabolism and growth rate of biofilm organisms which resist killing by compounds that only attack actively growing cells; 3) increased accumulation of antimicrobial-degrading enzymes; 4) enhanced exchange rates of drug resistance genes; and 5) increased antibiotic tolerance (as opposed to resistance) through expression of stress response genes, phase variation, and biofilm specific phenotype development (Fux et al. 2003. *Expert Rev. Anti. Infect. Ther.* 1: 667-683; Keren et al. 2004. *FEMS Microbiol. Lett.* 230: 13-18; Lewis, K. 2001. *Antimicrob. Agents Chemother.* 45: 999-1007; Hall-Stoodley et al. 2004. *Nat. Rev. Microbiol.* 2:95-108).

Biofilms also show heightened resistance to host defense mechanisms, such as, reduced activation of complement compared to planktonic cultures. Further, the aggregation of bacteria makes them less susceptible to phagocytosis (Cerca et al. 2005. *J. Antimicrob. Chemother.* 56: 331-336). Sub-inhibitory antibiotic concentrations can foster the formation of biofilms (Rachid et al., 2000. *Antimicrob. Agents*

Chemother. 44: 3357-3363). Hence, there is a need for enzymes to break down biofilms to optimize treatment of biofilm-associated staphylococcal infections (Otto, M. 2006. Curr. Top. Microbiol. Immunol. 306: 251-258).

Protein transduction domains facilitate translocation of full length proteins across the plasma membrane. Short amino acid sequences (13-20 residues) within eukaryotic proteins have been identified that can facilitate the movement of full length mature proteins into the cytoplasm from outside the cell. Some protein transduction domains (PTDs) or cell penetrating peptides (CPPs) are briefly described in Table 1 (Kabouridis, P. S. 2003. Trends Biotechnol. 21: 498-503). Synthetic PTDs have also been created, e.g., poly R or L.

The exact translocation mechanism for each construct is believed to rely on both the cell type being transduced, the domain type being utilized, and the size of the transduced fusion, with the literature reporting examples of both energy dependent and non-energy dependent, pinocytotic and non-pinocytotic mechanisms (Kabouridis, supra; Fotin-Mleczek et al. 2005. Curr. Pharm. Des. 11: 3613-3628). The translocation mechanism likely depends in part on ionic interactions between the basic groups of the amino acid side chains of the PTDs and negative charges associated with the plasma membrane.

TABLE 1

Protein Transduction Domains (PTD)

| Protein | PTD Amino Acid Sequence |
|---|---|
| Cationic: | |
| HIV-1 TAT (47-57) | YGRKKRRQRRR |
| Drosophila Antenapedia (43-58) | RQIKIWFQNRRMKWKK |
| Polyarginine (R7) (Synthetic) | RRRRRRR |
| PTD-5 (Synthetic) | RRQRRTSKLMKR |
| Amphipathic: | |
| Transportan (Chimeric gelatin/mastoparan) | GWTLNSAGYLLGKINL KALAALAKKIL |
| KALA (Synthetic) | WEAKLAKALAKALAKH LAKALAKALKACEA |

Despite the lack of a single mechanism, there are specific examples where the domain has allowed the transduced 'cargo' to achieve access to mitochondria (Rapoport et al. 2008. Mol. Ther. 16: 691-697), golgi apparatus (Fischer et al. 2004. J. Biol. Chem. 279: 12625-12635), endosomes (Vendeville et al. 2004. Mol. Biol. Cell. 15: 2347-2360), nuclear localization (Peitz et al. 2002. Proc. Natl. Acad. Sci. USA 99: 4489-4494; Bosnali and Edenhofer. 2008. Biol. Chem. 389: 851-861) and virtually all tested cytosolic compartments. Numerous studies have indicated that in mouse models, PTD fusions successfully transduce heart, liver, kidney, brain, lung and spleen when injected into mice (Jo et al. 2001. Nat. Biotechnol. 19: 929-933; Schwarze et al. 1999. Science 285: 1569-1572).

S. aureus has a high negative impact worldwide as both an extracellular and intracellular multi-drug resistant pathogen for humans, e.g., MRSA, and as an organism responsible for causing multiple animal diseases, e.g. mastitis, an infection of dairy cattle mammary glands. There is a need to develop pathogen-specific agents which have extracellular and intracellular activity as an approach for control of chronic staphylococcal mastitis, intracellular MRSA, and other gram positive pathogens.

SUMMARY OF THE INVENTION

We have discovered that a fusion polypeptide comprising lysostaphin, a protein that specifically digests the peptidoglycan cell wall and lyses live, untreated S. aureus, and a protein transduction domain (PTD), which facilitates translocation of full length proteins across the eukaryotic cell plasma membrane into the eukaryotic cytoplasm from outside the cell, can be used as an effective antimicrobial treatment for both extracellular and intracellular infections caused by S. aureus, by multidrug-resistant staphylococci, and other gram positive pathogens.

In accordance with this discovery, it is an object of the invention to provide a fusion protein comprising lysostaphin and a PTD.

It is also an object of the invention to provide an antimicrobial lysostaphin-PTD composition which is can degrade the peptidoglycan cell wall of intracellular Staphylococcus aureus including MRSA.

An added object of the invention is to provide a lysostaphin-PTD fusion polypeptide according to the invention, which allows both extracellular and intracellular Staphylococcus-induced disease and infection to be treated, including those caused by MRSA.

An added object of the invention is to provide PTD-containing fusion proteins useful for the treatment of diseases and infections caused by intracellularly located bacteria for which lysostaphin is specific.

Also part of this invention is a kit, comprising a lysostaphin-PTD fusion protein for treatment of chronic disease caused by extracellular and intracellular S. aureus, MRSA, and other Gram positive pathogens.

Other objects and advantages of this invention will become readily apparent from the ensuing description.

BRIEF DESCRIPTION OF THE DRAWINGS

FIG. 3 depict the staphylolytic activity of Lysostaphin-PTD fusion on internalized S. aureus in media (FIG. 3A) and milk (FIG. 3B). Bovine mammary epithelial cells (MAC-T) were cocultured with S. aureus Newbould 305 for 1 h at 37° C. After incubation, monolayers were washed 3× with PBS (pH 7.4) and incubated with lysostaphin (5 μg/ml Sigma) for 1 h at 37° C. to kill extracellular S. aureus. After incubation, monolayers were washed 3× with PBS (pH 7.4) to remove lysostaphin and incubated with increasing doses (1-100

µg/ml) of Lysostaphin-PTD for either (FIG. 3A) 1 h at 37° C. in DMEM media or (FIG. 3B) 2 hrs. at 37° C. in sterile milk (Parmalat). After incubation, monolayers were washed 3× with PBS (pH 7.4) and monolayer lysed with trypsin (0.05%) and triton (0.25%) in water. CFU/ml of *S. aureus* in final lysates were determined by dilution plating. FIG. 3A. Data are presented as CFU/ml. Bars correspond to the standard error of the mean (SEM) of 4 observations run in duplicate. FIG. 3B inoculum was $1.5 \times 10^6$ CFU/ml.

DETAILED DESCRIPTION OF THE INVENTION

The increased incidence of bacterial antibiotic resistance has led to a renewed search for novel antimicrobials. *S. aureus* has a high negative impact worldwide as both an extracellular and intracellular multi-drug resistant pathogen for humans, e.g., MRSA, and as an organism responsible for causing multiple animal diseases, e.g. mastitis, an infection of dairy cattle mammary glands.

Many bacterial pathogens are known to invade host cells and to reside there indefinitely, resulting in chronic infections. The barrier provided by the host cell membrane is believed to provide heightened protection from conventional antibiotics. Multi-drug- and methicillin-resistant *Staphylococcus aureus* (MRSA) can reside intracellularly, for example, in human osteomyelitis, where *S. aureus* infects bone progenitor cells. Bovine mastitis is another disease, where the pathogen invades mammary epithelial cells and immune cells (e.g., macrophages, polymorphonuclear neutrophilic leukocytes [PMNs]), or ventilator associated pneumonia where *S. aureus* can also invade immune cells (e.g., lung macrophages). Staphylococcal pathogens, *S. aureus* and CoNS, account for up to 40% of the bovine mastitis in the USA. Most *S. aureus*-infected cattle are culled, due to the highly contagious nature of these infections, creating an additional burden on the dairy industry. An effective treatment for intracellular staphylococcal infections would be of significant economic benefit to both human health and the dairy industry worldwide.

Peptidoglycan hydrolases have the added advantage that they often show near-species specificity in their peptidoglycan substrate. Lysostaphin is known to be highly specific to *S. aureus*. The lysins rarely target unrelated species, further reducing the risk of resistance development in non-targeted commensal strains, as often occurs with broad-spectrum antibiotics.

Figure 3:
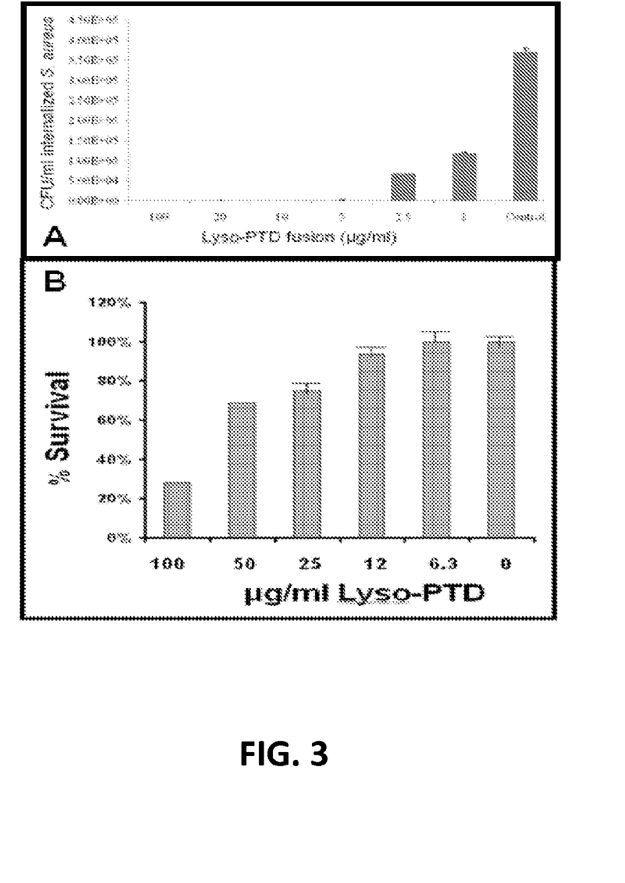

This invention expands on the staphylolytic properties of lysostaphin by adding a ~13 amino acid protein transduction domain (PTD) from the HIV-TAT protein. The addition of the PTD to the peptidoglycan hydrolase will still allow eradication of extracellular *S. aureus*, but will also kill intracellular forms of the pathogen. As a first demonstration of this technology, lysostaphin was fused to the TAT-PTD. Lysostaphin is a peptidoglycan hydrolase bacteriocin secreted by *S. simulans* that digests the peptidoglycan pentaglycine bridge of *S. aureus* (presumably killing the competition, gives an advantage to *S. simulans* in a nutrient limiting environment). In FIG. 3, one hour of treatment with TAT-Lysostaphin (SEQ ID NO:2) (5 ug) is sufficient to eradicate intracellular *S. aureus* from cultured MAC-T mammary epithelial cells. The control sample was only treated with extracellular lysostaphin and indicates that there were initially over $3.5 \times 10^5$ intracellular *S. aureus* in each sample.

In order to further demonstrate that the TAT-Lysostaphin fusion can also kill extracellular *S. aureus*, intracellular *S. aureus* was extracted from infected MAC-T cells and cultured in Todd-Hewitt broth (rich media). At mid log phase of growth, the bacterial culture was exposed to various concentrations of TAT-Lysostaphin. In FIG. 3, only 6 ug for a 1 hour exposure is required for the TAT-Lysostaphin fusion protein to kill $10^8$ *S. aureus* from broth cultures.

Staphylococci cause up to 40% of the bovine mastitis in the USA. Most can become chronic when they invade and reside intracellularly. We anticipate that through the use of PTDs, we have an antimicrobial with the potential to cure 40% of the bovine mastitis in the US, including chronic infections. Currently, there are no treatments for intracellular staphylococcal infections, once infected chronically, the cattle are routinely culled from the herd as a means to protect the remainder of the herd from this highly contagious pathogen.

Chronic intracellular staphylococcal infections similarly affect other cell types. For example, there are no good treatments for intracellular staphylococcal infections of human bone cells (osteomyelitis); *S. aureus* is responsible for 80% of human osteomyelitis (Ellington, at al. 2006. *J. Orthop. Res.* 24: 87-93; Webb et al. 2007. *J. Surg. Orthop. Adv.* 16: 73-78). Currently these infections can arise up to 8 months post trauma and are chronic. Staphylococcal infections of human bone cells are the most prevalent recurring infection for the troops returning from war zones in Afghanistan, and Iraq. In addition, colonization of human skin by *S. aureus* is a characteristic feature of several inflammatory skin diseases, which is often followed by tissue invasion and severe cell damage (Mempel et al. 2002. *Br. J. Dermatol.* 146: 943-951). The presence of intracellular *S. aureus* small colony variants in keratinocytes protect against host defenses and antibiotic therapy, thus contributing to prolonged skin infections (von Eiff at al. 2001. *Clin. Infect Dis.* 32: 1643-1647). Endothelial cells are yet another cell type targeted by invading intracellular *S. aureus* (Sinha and Herrmann. 2005. *Thromb. Haemost.* 94: 266-277).

It is feasible that peptidoglycan hydrolases that degrade other species can be similarly engineered to target other extracellular and intracellular gram positive pathogens e.g. Ply500 or Ply118 for *Listeria monocytogenes*.

According to the present invention, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof. This will also include a DNA sequence for which the codons encoding the lysostaphin-PTD according to the invention will have been optimized according to the host organism in which it will be expressed, these optimization methods being well known to those skilled in the art.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "construct" refers to a recombinant nucleic acid, generally recombinant DNA, that has been generated for the purpose of the expression of a specific nucleotide sequence(s), or is to be used in the construction of other recombinant nucleotide sequences. A "construct" or "chimeric gene construct" refers to a nucleic acid sequence encoding a protein, operably linked to a promoter and/or other regulatory sequences.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter) or a DNA sequence and a regulatory sequence(s) are connected in such a way as to permit gene expression when the appropriate molecules (e.g., transcriptional activator proteins) are bound to the regulatory sequence(s).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter.

The term "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein. "cDNA" refers to a DNA that is complementary to and derived from an mRNA template.

As used herein, "recombinant" refers to a nucleic acid molecule which has been obtained by manipulation of genetic material using restriction enzymes, ligases, and similar genetic engineering techniques as described by, for example, Sambrook et al. 1989. *Molecular Cloning: A Laboratory Manual*, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

A "protein" or "polypeptide" is a chain of amino acids arranged in a specific order determined by the coding sequence in a polynucleotide encoding the polypeptide. Each protein or polypeptide has a unique function.

The invention includes functional lysostaphin, lysostaphin-PTD, and lysostaphin-His polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of lysostaphin" refers to all fragments of lysostaphin that retain lysostaphin activity and function to lyse staphylococcal bacteria.

Modifications of the primary amino acid sequence of lysostaphin may result in further mutant or variant proteins having substantially equivalent activity to the lysostaphin polypeptides described herein. Such modifications may be deliberate, as by site-directed mutagenesis, or may occur by spontaneous changes in amino acid sequences where these changes produce modified polypeptides having substantially equivalent activity to the lysostaphin polypeptide. Any polypeptides produced by minor modifications of the lysostaphin primary amino acid sequence are included herein as long as the biological activity of lysostaphin is present; e.g., having a role in pathways leading to lysis of staphylococcal bacteria.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. Nucleic Acid Hybridization, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. An indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Thus, isolated sequences that encode a lysostaphin, lysostaphin-PTD, or lysostaphin-his polypeptide and which hybridize under stringent conditions to the lysostaphin, lysostaphin-PTD, or lysostaphin-his sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have lysostaphin-, lysostaphin-PTD-, or lysostaphin-his-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the lysostaphin, lysostaphin-PTD, or lysostaphin-his polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, lysostaphin, lysostaphin-PTD, or lysostaphin-his activity as described herein. Such variants may result from, for example, genetic polymorphism or from human manipulation. Biologically active variants of a native lysostaphin protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired lysostaphin, lysostaphin-PTD, or lysostaphin-his activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of lysostaphin, lysostaphin-PTD, or lysostaphin-his protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

The staphylococcal control compositions of the invention comprise the antimicrobial composition of the invention dissolved or suspended in an aqueous carrier or medium. The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The preferred compositions of this invention comprise ingredients which are generally regarded as safe, and are not of themselves or in admixture incompatible with milk or milk by-products or human and veterinary applications. Likewise, ingredients may be selected for any given composition which are cooperative in their combined effects whether incorporated for antimicrobial efficacy, physical integrity of the formulation or to facilitate healing and health in medical and veterinary applications, including for example in the case of mastitis, healing and health of the teat or other human or animal body part. Generally, the composition comprises a carrier which functions to dilute the active ingredients and facilitates stability and application to the intended surface. The carrier is generally an aqueous medium such as water, or an organic liquid such as an oil, a surfactant, an alcohol, an ester, an ether, or an organic or aqueous mixture of any of these, or attached to a solid stratum such as colloidal gold. Water is preferred as a carrier or diluent in compositions of this invention because of its universal availability and unquestionable economic advantages over other liquid diluents.

Avoiding the generalized use of broad range antimicrobials and using highly specific antimicrobials for just the target organisms or closely related species, should help reduce the ever-increasing incidence of antibiotic resistance.

EXAMPLES

Having now generally described this invention, the same will be better understood by reference to certain specific examples, which are included herein only to further illustrate the invention and are not intended to limit the scope of the invention as defined by the claims.

Example 1

Plasmids, Constructs and Strains

All subcloning was performed in *E. coli* DH5α (Invitrogen, Carlsbad, Calif.) for plasmid DNA isolation and sequence verification of all constructs. pET21a constructs were induced in *E. coli* BL21(DE3) (EMD Biosciences, San Diego, Calif.). *Staphylococcus aureus* Newbolt 305 capsular polysaccharide serotype 5 (ATCC 29740), *S. aureus* UAMS-1 (ATCC 49230), *S. aureus* strain Newman, and the MRSA strains: NRS194, NRS 271, and NRS 384 were grown at 3TC in Brain Heart Infusion broth (BD, Sparks, Md.) or Tryptic Soy Broth (BD, Sparks, Md.).

Example 2

PCR Cloning

PCR cloning was used to create the Lyso-PTD construct. The reverse PCR primer Lyso-TAT-XhoR (5'-GTG GTG CTCGAG GCG GCG GCG CTG GCG GCG TTT TTT GCG CTT TAT AGT TCC-3' (SEQ ID NO: 5) containing sequences encoding a 9 amino acid derivative (italics) of the 13 amino acid HIV-TAT PTD sequence (Table I), the last four codons (bold) of the C-terminus of the lysostaphin gene and an engineered XhoI site (underlined), together with a generic pET21a forward primer harboring an NdeI site at the translational start site, were used to amplify just the mature lysostaphin (256 aa) in a pET21a derived vector. The amplified Lyso-PTD DNA fragment was restriction enzyme digested (XhoI and NdeI) and ligated into similarly digested pET21a using conventional molecular techniques. BL21(DE3) *E. coli* (EMD Biosciences, San Diego, Calif.) were transformed with the characterized ligated coding sequences (SEQ ID NO:1) and the expressed protein products were purified (SEQ ID NO:2).

Example 3

Extract Preparation and Protein Purification

*E. coli* BL21(DE3) cells harboring plasmid constructs were grown in 500 ml Superbroth (Becton Dickenson, Franklin Lakes, N.J.) supplemented with 100 ug/ml ampicillin at 37° C. with shaking. At mid log phase ($OD_{600nm}$ of 0.4-0.6), cultures were induced with 1 mM IPTG (isopropyl-beta-D-thiogalactopyranoside) followed by four hours shaking at 37° C. Cells were pelleted, washed with lysis buffer (50 mM $NaH_2PO_4$, 300 mM NaCl, 10 mM Imidazole, pH 8) and pellets frozen at −80° C. Extracts were prepared according to a modified procedure of Pritchard et al. (2004. *Microbiology* 150: 2079-2087). For nickel column-purified protein, cell pellets from 500 ml cultures were resuspended in 10 ml lysis buffer (50 mM $NaH_2PO_4$, 300 mM NaCl, 10 mM Imidazole, pH 8) and disrupted with 15×10 second pulses of sonication on ice with 10 second rest periods between pulses. Lysates were centrifuged at 6800 rpm in a Sorvall HS4 rotor (8500×g) and the supernatant decanted and added to 5 ml Ni-NTA (nickel matrix) slurry per manufacturer's instructions (Qiagen, Valencia, Calif.) with gentle rocking for 1 hour at 4° C. The matrix was washed and protein eluted according to the manufacturer's instructions. Protein eluates were desalted in Micro Bio-Spin 30 columns (BioRad) prior to protein determination with BCA protein assay (Pierce, Rockford, Ill.).

The various protein fractions and Kaleidoscope protein standards (Invitrogen, Carlsbad, Calif.) were analyzed by SDS-polyacrylamide gel electrophoresis (SDS-PAGE). Proteins were loaded on 15% SDS-polyacrylamide gels and run in Tris-Glycine buffer at 131 volts for 1.5 hours in the BioRad Mini-PROTEAN 3 gel apparatus, according to the manufacturer's instructions. Gels were stained in BioSafe Coomassie stain (BioRad, Hercules, Calif.) for one hour and then rinsed in distilled water overnight.

Figure 2:
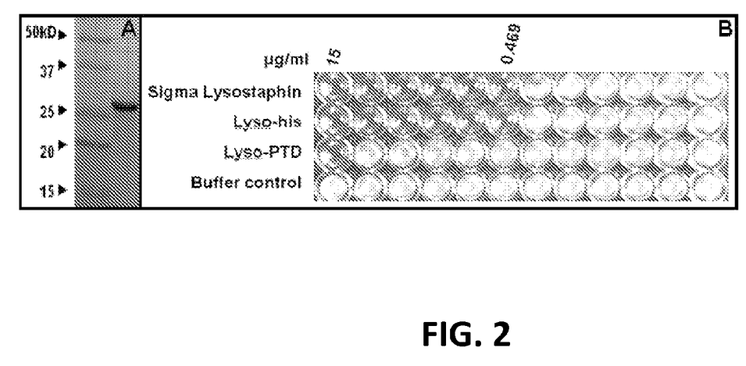
FIG. 2A depicts an SDS PAGE and reveals a pure Lyso-PTD nickel column-purified protein with the expected MW of 29.5 kDa.
FIG. 2B depicts a representative Minimum Inhibitory Concentration (MIC; the lowest concentration of lysin that prevents growth in 20 hrs) assay of Lyso-PTD on S. aureus strain Newman. The average MIC obtained from dual experiments for multiple S. aureus strains is presented in Table 2. Two fold dilutions of the lysin were made, starting from the first well. The MIC is noted above the appropriate well.

A Coomassie stained SDS-PAGE of the nickel chromatography-purified protein C-His-Lyso-PTD indicates the quality of the nickel column purification (FIG. 2A). SDS-PAGE reveals a pure Lyso-PTD nickel column-purified protein having an expected MW of 29.5 kDa.

Activity was demonstrated in turbidity reduction (data not shown), and Minimum Inhibitory Concentration (MIC) assays (FIG. 2B).

Example 4

Minimum Inhibitory Concentration

A classical microdilution broth method for determination of the Minimal Inhibitory Concentration (MIC) was used (Jones et al. 1985. In *Manual of Clinical Microbiology*, Balows of al. (Eds.), American Society for Microbiology, Washington D.C., pages 972-977). MIC determinations for numerous *S. aureus* strains including strain Newman (FIG. 2B), NRS 194, NRS 271, and MRSA NRS 384 (Table 2) were performed. Briefly, logarithmic-phase bacteria were cultivated in tryptic soy broth and adjusted in broth to a concentration of $1 \times 10^6$ CFU/ml. Sterile 96 well microtiter plates containing 100 µl of either Lysostaphin (recombinant, Sigma-Aldrich, L0761), Lysostaphin-His (SEQ ID NO: 4), or Lysostaphin-PTD (SEQ ID NO:2) diluted in TSB are inoculated with 100 µl of the bacterial suspension to yield $5 \times 10^5$ CFU/ml. The plate is incubated at 37° C. for 20 h, at which point the plate is analyzed for clear vs. turbid wells. Each MIC assay represents at least two identical determinations per experiment.

TABLE 2

Minimum Inhibitory Concentration (µg/ml) of lysostaphin-derived constructs.

| Lysin | NRS 194 | NRS 271 | NRS 384 | Newman |
|---|---|---|---|---|
| Lysostaphin (Sigma) | 0.332 | 0.078 | 0.332 | 0.142 |
| Lyso-his | 0.430 | 0.312 | 0.430 | 0.430 |
| Lyso-PTD | 13.750 | 10.000 | 13.750 | 10.000 |

NRS 194 (Community acquired *S. aureus*, C1999000529)
NRS 271 (*S. aureus*, Linezolid-resistant)
NRS 384 (MRSA, USA300-0114)

Lysostaphin constructs inhibit extracellular growth of multiple *S. aureus* strains (including MRSA). Lysostaphin (Sigma) inhibits *S. aureus* growth at an MIC between 0.078-0.332 µg/ml and Lysostaphin-PTD yields an MIC between 10-13.75 µg/ml with the Lyso-His MIC lying intermediate between these two extremes (Table 2.; FIG. 2B).

Example 5

Effect of Lysostaphin-PTD on Internalized *S. aureus* in Cultured Mammary Cells

Bovine mammary epithelial cells (MAC-T) were cocultured with *S. aureus* Newbould 305 (MOI 10:1) in 24 well dishes for 1 h at 37° C. After incubation, monolayers were washed 3× with PBS (pH 7.4) and incubated with lysostaphin (5 µg/ml) for 1 h at 37° C. to kill extracellular *S. aureus*. After incubation, monolayers were washed 3× with PBS (pH 7.4) to remove lysostaphin and incubated with increasing doses (1-100 µg/ml) of Lysostaphin-PTD for either 1 h at 37° C. in DMEM media (FIG. 3A) or 2 hrs. at 37° C. in sterile milk (Parmalat) (FIG. 3B). After incubation, monolayers were washed 3× with PBS (pH 7.4) and lysed with trypsin (0.05%) and triton (0.25%) in water. CFU/ml of *S. aureus* in final lysates were determined by dilution plating.

Lyso-PTD can kill intracellular *S. aureus*-cultured MAC-T cells in both media and milk. The MIC for lysostaphin is within the published range. The addition of the PTD increases the lysostaphin MIC four fold. Lyso-PTD kills both extracellular (data not shown) and internalized *S. aureus* in cultured mammary epithelial cells.

Example 6

Effect of Lysostaphin-PTD on Internalized *S. aureus* in Cultured Osteoblasts

Primary murine osteoblast cell cultures were prepared from C57BL/6 by sequential collagenase-protease digestion as described previously (Marriott et al. 2005. *Bone* 37: 504-512). Osteoblasts isolated in this manner have previously been characterized as being >99% pure cultures as determined by their distinctive morphology, and by the expression of type I collagen, osteocalcin, alkaline phosphatase, and parathyroid hormone-cAMP. All experiments were performed on osteoblasts grown to the point of confluency in six well plates or culture flasks, and comparisons were made between the treatment groups in each experimental series to ensure equal cell numbers. Confluent cell layers of cells were exposed to *S. aureus* UAMS-1 (ATCC 49230), a clinical isolate and capable of inducing inflammatory responses in osteoblasts, at the indicated ratios of bacteria to osteoblasts in growth medium without antibiotics for 45 min at 37° C. Following the infection period, cell cultures were washed with PBS and incubated in growth medium with 25 ug/ml gentamicin to kill remaining extracellular bacteria. At 24 hours following infection, infected cells were exposed to a LPS-free endolysin preparation (0.1, 1 or 10 ug/ml as determined by Bradford assay) for 4 hours prior to exposure of cells to 0.1% Triton-X100 for 5 min at 3TC to liberate intracellular bacteria. Bacteria were then washed and enumerated by serial dilution plate counting.

Figure 4:
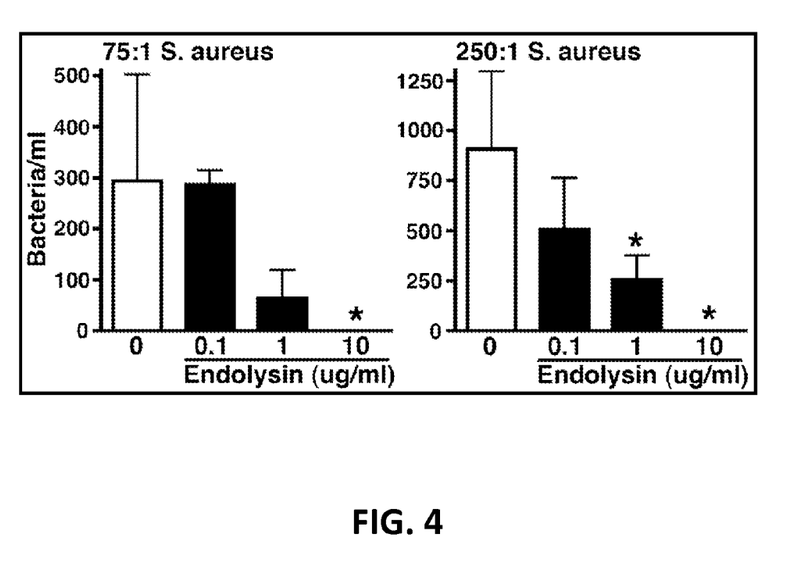
FIG. 4 depicts the killing of intracellular *S. aureus* in primary murine osteoblasts by Lyso-PTD.

Lyso-PTD can kill intracellular *S. aureus* in primary murine osteoblasts. Data shown are presented as the mean of three experiments+/−SEM at two different multiplicity of infection (M01) 75:1 and 250:1 (FIG. 4).

Example 7

Effect of Lysostaphin-PTD on Internalized *S. aureus* in Cultured Brain Endothelium Cells

*S. aureus* wild-type strain ISP479C was grown to $OD_{600}$=0.4 at 37° C. in 4 mL LB broth. The culture was centrifuged at 4,000 rpm for 5 min to pellet cells. The cell pellet was resuspended in 200 μL sterile DPBS and used to bring 3 mL sterile PBS to $OD_{600}$=0.4. Serial dilutions were made of the 3 mL cell suspension and plated on LB agar to determine the initial cfu/mL. Brain endothelium (hBMEC) cells in a monolayer in 24-well TC plates were washed 3× with sterile PBS before the addition of 0.4 mL RPMI without antibiotics. *S. aureus* culture was added to each well to achieve either an M01=1 or 0.1 (100 uL of −2 dilution for MOI=1 or 100 uL of −3 dilution for MOI=0.1). Plates were spun down briefly before being returned to the incubator (5% $CO_2$ at 37° C.) for 90 min. Following this incubation cell monolayers were washed 3× with sterile PBS before the addition of 0.5 mL RPMI+50 μg/mL gentamycin. Cells were returned to the incubator for 45 min. Following incubation monolayers were washed 3× with DPBS before the addition of 0.5 mL RPMI+0, 10, 25 or 50 μg lysostaphin (or the equivalent volume of a 30% glycerol/DPBS solution as a control). Plates were incubated for 60 min then washed 3× with DPBS before the addition of 100 μl. trypsin and 400 μL Triton-X. Cell lysates were diluted and 25 μL volumes plated onto LB agar.

Figure 5:
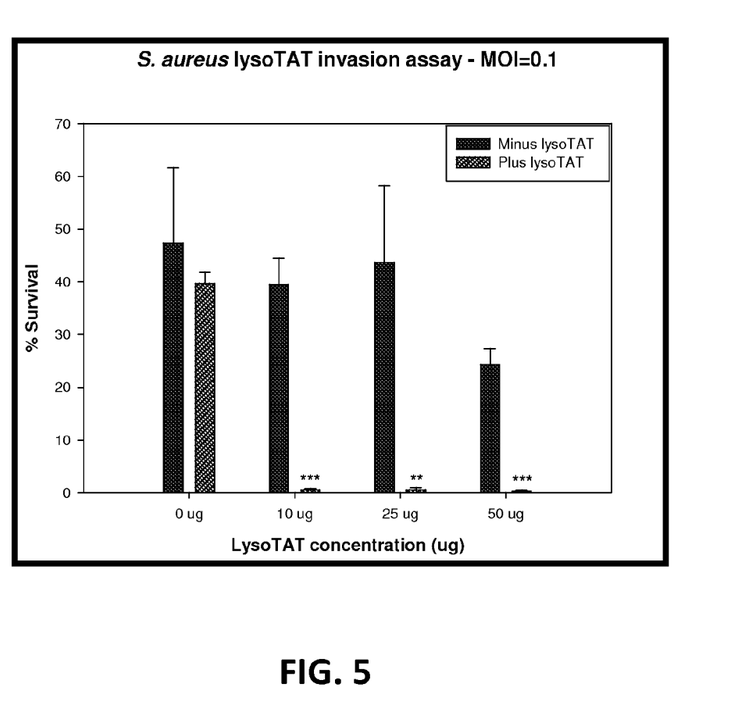
FIG. 5 shows that Lyso-PTD can kill intracellular *S. aureus* in human brain endothelium cells.
Figure 6:
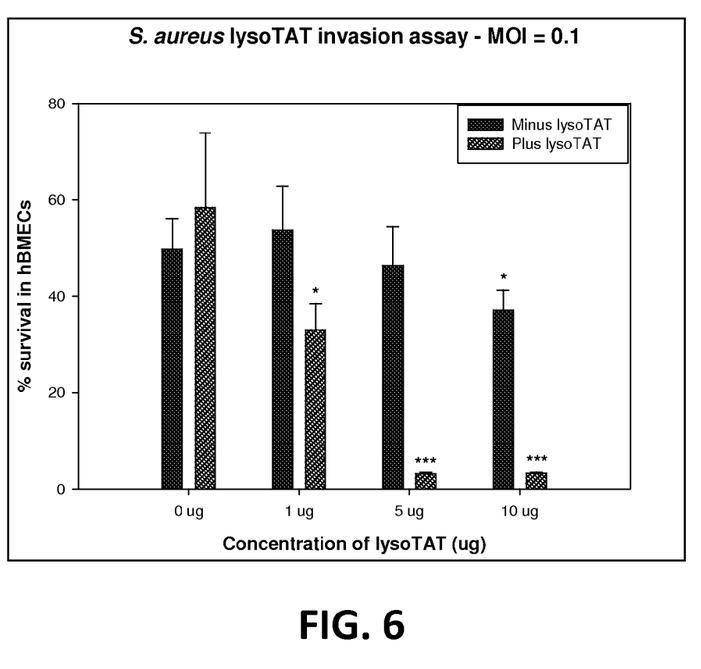
FIG. 6 shows that Lyso-PTD can kill intracellular *S. aureus* in human brain endothelium cells—same protocol but different concentrations as FIG. 5.

Lyso-PTD can kill intracellular *S. aureus* in human brain endothelium cells (FIGS. 5 and 6; different concentrations). The P-value for the minus lyso-TAT sample at 50 μg vs 0 μg=0.053, indicating that there is a trend towards a significant difference in percent survival with the addition of higher concentrations of the glycerol/DPBS control solution.

Example 8

Effect of Lysostaphin-PTD on Internalized *S. aureus* in Cultured Human Keratinocytes

*S. aureus* wild-type strain ISP479C was grown to $OD_{600}$=0.4 at 37° C. in 4 mL LB broth. The culture was centrifuged at 4,000 rpm for 5 min to pellet cells. The cell pellet was resuspended in 200 uL sterile DPBS and used to bring 3 mL sterile DPBS to $OD_{600}$=0.4. Serial dilutions were made of the 3 mL cell suspension and plated on LB agar to determine the initial cfu/mL. Human keratinocytes (haCaT) cells in a monolayer in 24-well TC plates were washed 3× with sterile DPBS before the addition of 0.4 mL RPMI without antibiotics. *S. aureus* culture was added to each well to achieve an MOI=0.1 (100 uL of −3 dilution) for MOI=0.1). Plates were spun down briefly before being returned to the incubator (5% $CO_2$ at 37° C.) for 90 min. Following this incubation, cell monolayers were washed 3× with sterile DPBS before the addition of 0.5 mL RPMI+50 ug/mL gentamycin. Cells were returned to the incubator for 45 min. Following incubation monolayers were washed 3× with DPBS before the addition of 0.5 mL RPMI+0, 10, 25 or 50 μg lysostaphin (or the equivalent volume of a 30% glycerol/DPBS solution as a control). Plates were incubated for 60 min then washed 3× with DPBS before the addition of 100 μL trypsin and 400 μL Triton-X. Cell lysates were diluted and 25 μL volumes plated onto LB agar.

Figure 7:
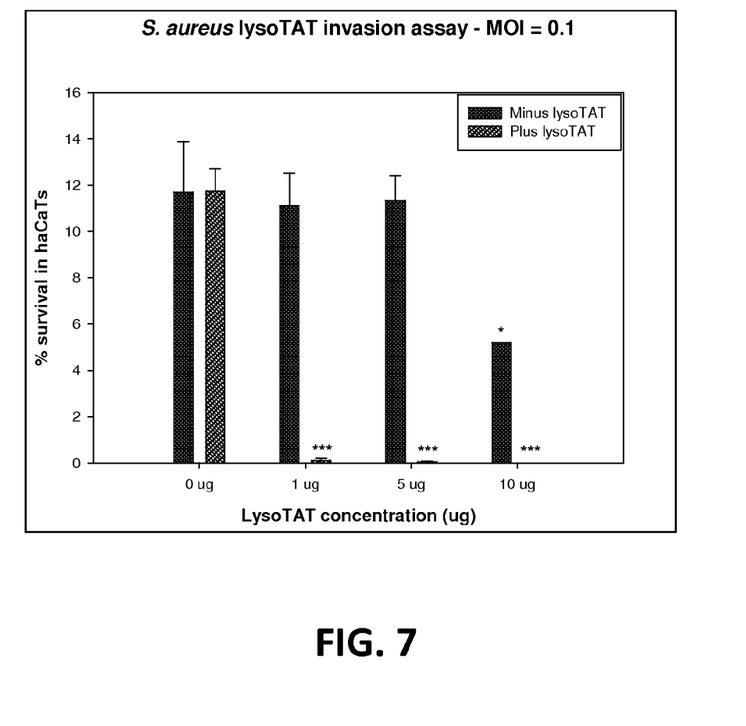
FIG. 7 depicts the killing of intracellular *S. aureus* in human keratinocytes (haCat) by Lyso-PTD.

Lyso-PTD can kill intracellular *S. aureus* in human keratinocytes (haCat) (FIG. 7).

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

I claim:

1. A recombinant nucleic acid encoding an antimicrobial lysostaphin fusion protein, comprising lysostaphin and a protein transduction domain(PTD), said fusion protein having lytic activity for the peptidoglycan cell wall resulting in bactericidal activity toward untreated, live intracellular and extracellular Staphylococcus aureus, including multi-drug resistant (MRSA), pathogens wherein said fusion protein comprises the polypeptide sequence of SEQ ID NO: 1.

2. The recombinant nucleic acid of claim 1 wherein the protein transduction domain is from the HIV-1-TAT protein.

3. The recombinant nucleic acid of claim 2 wherein said nucleic acid encodes a lysostaphin-PTD comprising a nucleic acid identified by SEQ ID NO: 1.

4. A construct comprising the nucleic acid of claim 3, wherein said nucleic acid is in operable linkage to a promoter that drives expression in a host cell.

5. A cloning vector comprising the construct of claim 4.

6. An expression vector comprising the construct of claim 4.

7. A process for transforming a host cell, comprising stably integrating the nucleic acid of claim 1 or the construct of claim 4 into the host cell.

8. An isolated host cell transformed with the nucleic acid according to claim 1.

9. An isolated host cell transformed with the construct according to claim 4.

10. A method of making a recombinant antimicrobial *Staphylococcus*-specific lysostaphin-PTD fusion protein, said method comprising steps:

a. introducing into a host cell a nucleic acid or construct encoding an antimicrobial *Staphylococcus*-specific lysostaphin-PTD fusion protein comprising SEQ ID NO: 2;

b. culturing said cell under conditions suitable for expression of said protein;

c. recovering the protein so expressed.

11. The protein of claim 10, wherein the fusion protein is a lysostaphin-PTD fusion protein.

12. A composition useful for the treatment of a disease caused by S. aureus or MRSA, wherein said composition comprises the protein of claim 11 and a pharmaceutically acceptable carrier.

13. A composition useful for the treatment of a disease caused by intracellular S. aureus or MRSA wherein said composition comprises the protein of claim 11 and a pharmaceutically acceptable carrier.

14. A method of treating an intracellular infection and disease caused by S. aureus or MRSA in an individual comprising:

administering to said individual an effective dosage of a composition of claim 13, wherein said composition comprises a recombinant antimicrobial *Staphylococcus*-specific lysostaphin-PTD fusion protein, said protein having lytic activity for the peptidoglycan cell wall resulting in bactericidal activity toward untreated, live intracellular and extracellular *Staphylococcus aureus*, including MRSA, pathogens, wherein said administration is effective for the treatment of said staphylococci in multiple cell types.

15. A method of treating mastitis in an animal comprising:

administering to said animal an effective dosage of a composition of claim 13, wherein said composition comprises a recombinant antimicrobial *Staphylococcus*-specific lysostaphin-PTD fusion protein, said protein having lytic activity for the peptidoglycan cell wall resulting in bactericidal activity toward untreated, live intracellular and extracellular *Staphylococcus aureus*, including MRSA, pathogens, wherein said administration is effective for reducing the severity of said mastitis.

* * * * *